United States Patent
Itkin et al.

(10) Patent No.: US 10,639,458 B2
(45) Date of Patent: May 5, 2020

(54) DEVICES AND METHODS FOR ALLEVIATING LYMPHATIC SYSTEM CONGESTION

(71) Applicants: THE TRUSTEES OF THE UNIVERSITY OF PENNSYLVANIA, Philadelphia, PA (US); THE CHILDREN'S HOSPITAL OF PHILADELPHIA, Philadelphia, PA (US)

(72) Inventors: Maxim Itkin, Bala Cynwyd, PA (US); Yoav Dori, Wynnewood, PA (US)

(73) Assignees: The Trustees of the University of Pennsylvania, Philadelphia, PA (US); The Children's Hospital of Philadelphia, Philadelphia, PA (US)

( * ) Notice: Subject to any disclaimer, the term of this patent is extended or adjusted under 35 U.S.C. 154(b) by 399 days.

(21) Appl. No.: 15/321,284

(22) PCT Filed: Jun. 26, 2015

(86) PCT No.: PCT/US2015/037983
§ 371 (c)(1),
(2) Date: Dec. 22, 2016

(87) PCT Pub. No.: WO2015/200797
PCT Pub. Date: Dec. 30, 2015

(65) Prior Publication Data
US 2017/0197066 A1    Jul. 13, 2017

Related U.S. Application Data

(60) Provisional application No. 62/017,613, filed on Jun. 26, 2014.

(51) Int. Cl.
*A61M 27/00*    (2006.01)
*A61M 39/24*    (2006.01)

(52) U.S. Cl.
CPC .......... *A61M 27/002* (2013.01); *A61M 39/24* (2013.01); *A61M 2202/0405* (2013.01); *A61M 2205/50* (2013.01)

(58) Field of Classification Search
CPC .............. A61M 27/002; A61M 27/006; A61M 27/008; A61M 39/24; A61M 39/26;
(Continued)

(56) References Cited

U.S. PATENT DOCUMENTS 4,714,460 A   12/1987   Calderon
5,836,912 A   11/1998   Kusleika
(Continued)

FOREIGN PATENT DOCUMENTS

WO   WO 2012/135834 A2   10/2012
WO   WO 2014/015377 A1   1/2014
WO   WO 2014/141284 A2   9/2014

OTHER PUBLICATIONS

U.S. Appl. No. 14/625,930 (US 2015-0343136), filed Feb. 19, 2015 (Dec. 3, 2015).
(Continued)

*Primary Examiner* — Philip R Wiest
(74) *Attorney, Agent, or Firm* — Baker Botts, LLP

(57) ABSTRACT

The presently disclosed subject matter relates to methods and devices for decompressing the lymphatic system. In particular, the present disclosure provides devices for actively or passively decompressing the lymphatic system and methods of their use and deployment within a subject. In certain non-limiting embodiments, a device of the present disclosure can include a pump for actively transferring lymph fluid from the lymphatic fluid into the venous system.

12 Claims, 12 Drawing Sheets

(58) Field of Classification Search
CPC .... A61M 2027/004; A61M 2202/0405; A61M 2205/50; A61F 9/00781
See application file for complete search history.

(56) References Cited

U.S. PATENT DOCUMENTS

| | | | |
|---|---|---|---|
| 6,616,623 B1 | 9/2003 | Kutushov | |
| 2004/0147871 A1 | 7/2004 | Burnett | |
| 2004/0230181 A1 | 11/2004 | Cawood | |
| 2009/0228059 A1 | 9/2009 | Shuros et al. | |
| 2010/0312164 A1* | 12/2010 | Forsell | B01D 46/0065 604/9 |
| 2011/0092955 A1 | 4/2011 | Purdy | |
| 2011/0282274 A1 | 11/2011 | Fulton et al. | |
| 2012/0029466 A1* | 2/2012 | Callaghan | A61B 5/0215 604/500 |
| 2013/0138041 A1 | 5/2013 | Smisson, III et al. | |
| 2013/0237954 A1 | 9/2013 | Shuros et al. | |
| 2013/0245607 A1* | 9/2013 | Eversull | A61M 1/3496 604/509 |
| 2013/0317535 A1 | 11/2013 | Demmy | |
| 2013/0338559 A1 | 12/2013 | Franano et al. | |
| 2014/0155806 A1 | 6/2014 | Cheng et al. | |
| 2014/0303461 A1 | 10/2014 | Callaghan et al. | |
| 2015/0343136 A1 | 12/2015 | Nitzan et al. | |
| 2015/0343186 A1 | 12/2015 | Nitzan et al. | |
| 2017/0197021 A1 | 7/2017 | Nitzan et al. | |

OTHER PUBLICATIONS

International Search Report and Written Opinion dated Dec. 8, 2015 in International Application No. PCT/US15/37983.
International Search Report and Written Opinion for International Patent Application No. PCT/IB2015/001658 dated Jan. 14, 2016.
International Search Report and Written Opinion for International Patent Application No. PCT/IB2015/001605 dated Jan. 13, 2016.
U.S. Appl. No. 14/625,930, Nov. 22, 2017 Response to Non-Final Office Action.
U.S. Appl. No. 14/625,930, Aug. 25, 2017 Non-Final Office Action.

* cited by examiner

Valved tube or tissue engineered valved graft deployed into a dilated TD outlet

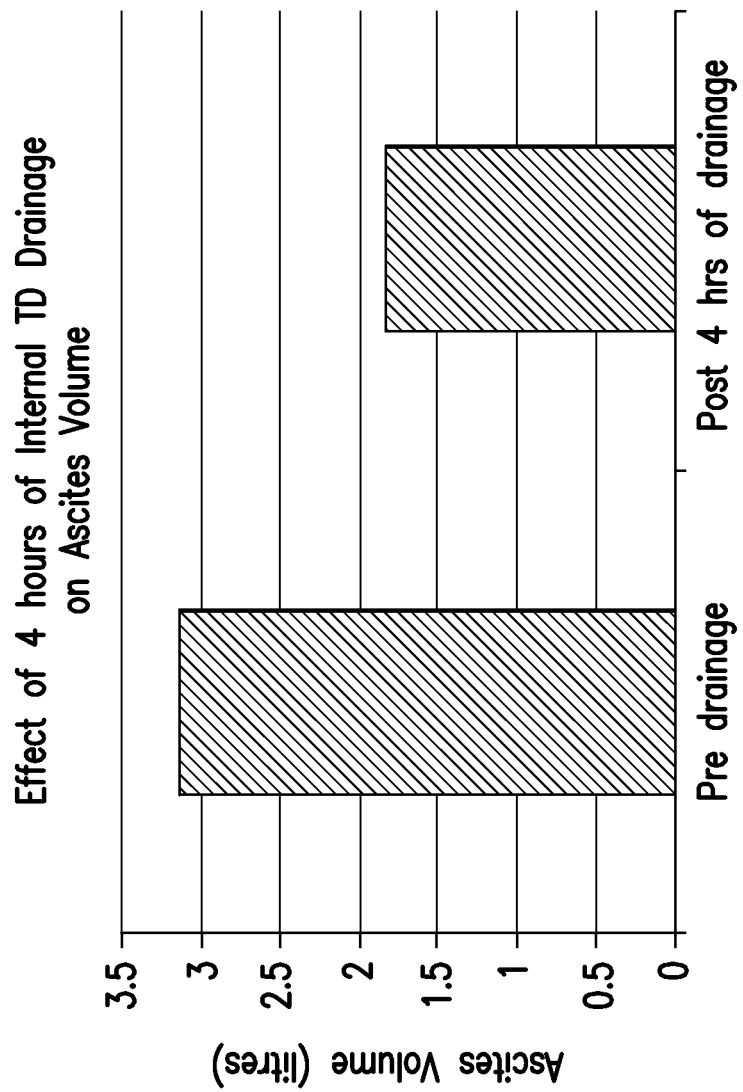

DEVICES AND METHODS FOR ALLEVIATING LYMPHATIC SYSTEM CONGESTION

CROSS-REFERENCE TO RELATED APPLICATIONS

This application is a U.S. National Stage Patent Application under 35 U.S.C. § 371 of International Application No. PCT/US2015/037983, filed on Jun. 26, 2015, which claims priority to U.S. Provisional Patent Application Ser. No. 62/017,613, filed Jun. 26, 2014, the contents of each of which are incorporated by reference herein in their entirety.

BACKGROUND

According to The National Heart, Lung and Blood Institute (NHLBI) there are approximately 5 million Americans living with congestive heart failure (CHF) and the prevalence of liver cirrhosis is estimated at 400,000 individuals. Both diseases are associated with significant morbidity and mortality. Abnormalities in lymphatic production and drainage are responsible for many symptoms in these diseases. In CHF, increased central venous pressure can lead to decreased lymphatic drainage and increased lymphatic production, which results in CHF symptoms such as tissue edema and liver enlargement. In patients with liver cirrhosis, increased pressure in the hepatic sinusoid can lead to significant increases in liver lymphatic production. When production overcomes the capacity of the system to drain, symptoms can appear in the form of ascites.

Most of the lymphatic fluid that originates in the tissue drains into the thoracic duct (TD), which is the biggest lymphatic vessel in the body. It has been shown that the TD can be significantly distended in patients with liver cirrhosis and CHF. The cause of TD distension is likely due to an increased production of the lymph and elevated TD pressure (1). It has been shown that in patients with CHF, external decompression of the TD can improve symptoms of CHF, such as dyspnea, orthopnea, anorexia, abdominal discomfort, distended neck veins, hepatomegaly, peripheral and scrotal edema and ascites (2, 3). Decompression of the TD has also been shown to resolve ascites in patients with liver cirrhosis (4). External drainage of the TD is invasive and can lead to significant metabolic, immunologic and fluid imbalances. Internal drainage of the TD can overcome these limitations and has been demonstrated to work in both animals and humans. For example, TD to subclavian vein anastomosis to resolve cirrhotic ascites has been described (5, 6). TD to pulmonary vein (PV) shunt has also been described but can require a complicated surgical procedure and its long-teen efficacy is unknown (7). One of the problems with passive decompression of the TD into the venous system is that in most patients with congestive heart failure the pressure in the central venous system is elevated and this increase in pressure has been shown to impede the flow from the TD into the venous system.

Therefore, there remains a need in the art for methods and devices for long-term decompression of the lymphatic system and to alleviate the symptoms associated with CHF and liver cirrhosis.

SUMMARY

The presently disclosed subject matter relates, in certain embodiments, to devices for decompressing the lymphatic system. The disclosed subject matter further relates, in certain embodiments, to methods for deploying such devices.

In certain embodiments, the disclosed subject matter relates to devices for reducing the congestion of the lymphatic system that include a pump. In certain embodiments, the devices of the present disclosure can further include a controller coupled to the pump. In certain embodiments, the devices of the present disclosure can include a sensor that can detect the changes in pressure, which can, in certain embodiments, be coupled to the controller. For example, and not by way of limitation, the sensor can detect a change or increase in pressure of the thoracic duct and/or central venous system. An increase in pressure detected by the sensor can result in the activation of the pump by the controller to remove lymph fluid from the lymphatic system. In certain embodiments, a device of the present disclosure can include a pressure controlled chamber for providing a favorable pressure gradient for the flow of lymph fluid from the lymphatic system and into the device. The pressure controlled chamber can be coupled to the pump and/or the controller.

In certain embodiments, the devices of the present disclosure can further include an access chamber, where the activation of the pump results in the flow of lymphatic fluid of the lymphatic system from the one or more pressure controlled chambers to the access chamber. The access chamber can be located internally, subcutaneously or externally and can function to remove the lymphatic fluid from the lymphatic system.

In certain embodiments, the devices of the present disclosure can further include one or more isolation valves. The one or more isolation valves can function to isolate the devices from blood of the venous system and/or prevent lymphatic fluid from entering the devices when drainage of the lymphatic fluid is not required.

The presently disclosed subject further relates to devices for passively reducing the congestion of the lymphatic system. In certain embodiments, such devices include a stent. In certain embodiments, the devices can further include a valve coupled to the stent. For example, but not by way of limitation, the valve can function to prevent the reflux of the blood from the venous system into the thoracic duct. In certain embodiments, the stent can be a self-expanding stent. In certain embodiments, the stent can be a bare stent, a covered stent or a combination thereof.

The presently disclosed subject further relates to methods for reducing the congestion of the lymphatic system. In certain embodiments, such methods include employing a tapered tubular member, such as, but not limited to, a catheter, that is coupled to a device as disclosed herein and guiding the coupled tubular member and device to a site of implantation; implanting the device at the site of implantation; and thereafter removing the tapered tubular member. In certain embodiments, the coupled tubular member can be guided through the venous system to the tubular duct outlet. In certain embodiments, the coupled tubular member can be guided through the venous system through the thoracic duct outlet and into the thoracic duct. In certain embodiments, the coupled tubular member can be guided through the thoracic duct to the thoracic duct outlet. In certain embodiments, the site of implantation can be the junction between the venous system and the tubular duct. In certain embodiments, the site of implantation can be under the skin. In certain embodiments, the device (or at least one component thereof) can be positioned on top of the skin of the subject. In certain embodiments, the device can be delivered transcutaneously directly into the thoracic duct.

BRIEF DESCRIPTION OF THE FIGURES

FIG. 8A-D depicts the effect active drainage has on lymphodynamics. (A) The pressure with the thoracic duct and innominate vein in a normal animal and the difference between them (ΔP=TD−innominate vein). As seen the pressure in the thoracic duct is not pulsatile and the ΔP is mostly negative. (B) In an animal with elevated central venous pressure (CVP) the thoracic duct pressure becomes pulsatile and ΔP is mostly positive representing significant lymphatic load. (C) After four (4) hours of internal thoracic duct drainage, thoracic duct tracing is almost normalized and ΔP is almost entirely negative representing favorable pressure gradients for tissue drainage. (D) The ascites volume was reduced after internal drainage of the thoracic duct.

DETAILED DESCRIPTION

The presently disclosed subject matter relates, in certain embodiments, to methods and devices for decompressing the lymphatic system. For example, in certain embodiments, the present disclosure relates to devices for either actively or passively decompressing the lymphatic system and methods for the deployment of such devices within a subject.

Figure 1A:
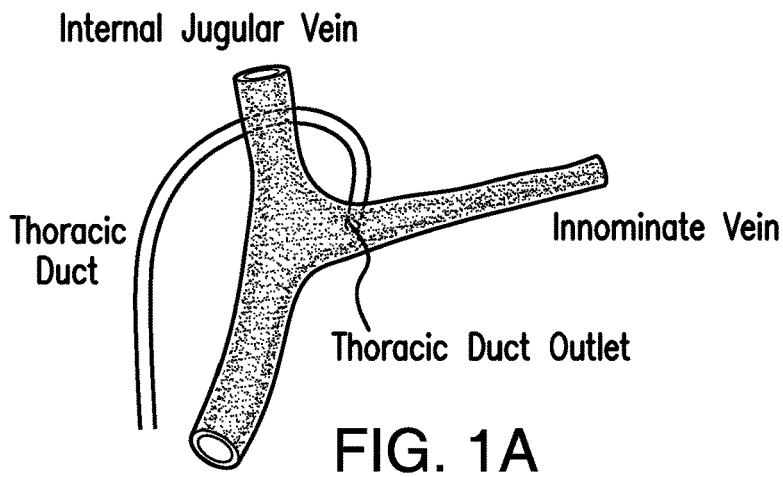
FIG. 1A-E depicts exemplary embodiments of devices for passively decompressing the lymphatic system according to the presently disclosed subject matter.

One of the functions of the lymphatic system is to remove the excessive interstitial fluid from bodily tissues and deliver it to the venous system. Fluid perfusion of the tissues involves the filtration of the fluid portion of the blood (i.e., plasma) through the arterial capillary network into interstitial tissue resulting in an accumulation of interstitial fluid. A large portion of the fluid within the tissues is returned (e.g., approximately 80%) to the venous system. The remaining fluid, i.e., lymph, can be removed from the tissues by the lymphatic system (e.g., approximately 20%). The lymphatic system returns this excessive fluid into the venous system through a valve at the junction of the thoracic duct and the innominate vein (see FIG. 1A).

Lymph production is governed by the Starling equation set forth in Formula 1:

$$Jv = Kf([PC-Pi] - \sigma[\pi C - \pi i]) \qquad \text{[Formula 1]}$$

Where Jv is the net fluid movement between compartments; Pc is the capillary hydrostatic pressure; Pi is the interstitial hydrostatic pressure; πc is the capillary oncotic pressure; πi is the interstitial oncotic pressure; Kf is the filtration coefficient (a proportionality constant); and σ is the reflection coefficient.

Lymphatic flow from tissue into the thoracic duct and then out of the thoracic duct outlet into the venous system is governed by the dynamic pressure gradients between the tissue and the thoracic duct and between the thoracic duct and the venous system as well as by the cross-sectional area available for fluid flow. This relationship can be described by the Hagen-Poiseuille equation set forth in Formula 2:

$$Q = \frac{\Delta P \cdot \pi r 4}{8 \mu L} \qquad \text{[Formula 2]}$$

Where r is the radius of the vessel or opening (e.g., duct) and ΔP is the pressure gradient.

In the absence of proper drainage of the lymphatic system into the venous system, congestion of the lymphatic system and central lymphatic failure can result. Central lymphatic failure can occur under circumstances where lymph production exceeds the lymphatic drainage capacity of the lymphatic system. This can occur in the setting of congestive heart failure where there is increased lymphatic production due to a shift in the Starling forces as well as inhibition of lymphatic drainage due to an elevated central venous pressure and a limited flow capacity of the thoracic duct outlet valve. In patients with liver cirrhosis, increased production of lymph in the liver can exceed the flow capacity of the thoracic duct outlet valve in the setting of normal central venous pressure resulting in central lymphatic failure.

Congestion of the lymphatic system leads to the accumulation of a watery fluid in the tissue causing tissue swelling and edema. Tissue edema in the lungs can lead to orthopnea and dyspnea, and tissue edema in the liver can lead to liver enlargement and dysfunction. Tissue edema can also interfere with wound healing and, if left untreated, can cause fibrosis. Fibrosis, which is a hardening of the tissue in the affected area, can further complicate the drainage process and can cause life-threatening conditions, such as infections.

Accordingly, the present disclosure relates, in certain embodiments, to devices and methods for alleviating the symptoms associated with lymphatic diseases and in conditions where drainage of the lymphatic system is needed such as, but not limited to, congestive heart failure, congenital heart disease, right-sided heart failure, Noonan syndrome, Turner syndrome, liver cirrhosis, lymphatic disease such as Gorham's disease, Lymphangioleiomyomatosis, lymphangiectasia, multiple sclerosis, Human immunodeficiency virus (HIV), autoimmune diseases, rheumatologic diseases such as rheumatoid arthritis, infectious diseases other than HIV, Systemic inflammatory response syndrome (SIRS), Acute respiratory distress syndrome (ARDS), lung disease, immune deficiencies, cancer and during cancer therapy. The present disclosure further relates, in certain embodiments, to methods for implanting such devices.

Definitions

Unless otherwise defined, all technical and scientific terms used herein have the same meanings as commonly understood by one of ordinary skill in the art.

An "individual," "patient" or "subject," as used interchangeably herein, can be a human or non-human animal. Non-limiting examples of non-human animal subjects include non-human primates, dogs, cats, mice, rats, guinea pigs, rabbits, pigs, fowl, horses, cows, goats, sheep and cetaceans.

The term "about" or "approximately" means within an acceptable error range for the particular value as determined by one of ordinary skill in the art, which will depend, in part, on how the value is measured or determined, i.e., the limitations of the measurement system. For example, "about" can mean within 3 or more than 3 standard deviations, per the practice in the art. Alternatively, "about" can mean a range of up to +/−20%, up to +/−10%, up to +/−5%, and up to +/−1% of a given value. Alternatively, particularly with respect to biological systems or processes, the term can mean within an order of magnitude, e.g., within 5-fold or within 2-fold, of a value.

The term "coupled," as used herein, refers to the connection of a device component to another device component by any means known in the art. The type of coupling used to connect two or more device components can depend on the scale and operability of the device. For example, and not by way of limitation, coupling of two or more components of a device disclosed herein can include one or more joints, valves, fittings, couplings, transfer lines or sealing elements.

Devices

In certain embodiments, the present disclosure relates to devices that decompress the lymphatic system to alleviate the symptoms associated with central lymphatic failure. Accordingly, the present disclosure relates, in certain embodiments, to devices for either actively or passively reducing congestion of the lymphatic system by alleviating unfavorable pressure gradients and/or the limited flow capacity of the thoracic duct outlet value.

Devices for Passive Decompression of the Lymphatic System

In certain embodiments, devices according to the disclosed subject matter can be used to decompress the lymphatic system by providing structural support to the thoracic duct, e.g., the terminal thoracic duct, to increase and/or enhance the flow capacity of the thoracic duct.

Figure 1B:
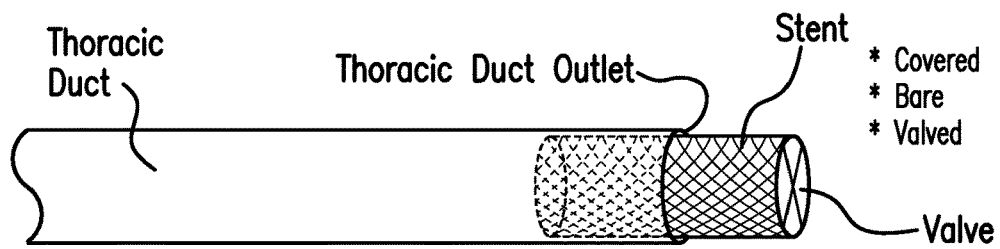
Figure 1C:
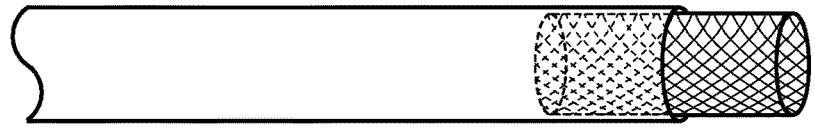
Figure 1D:
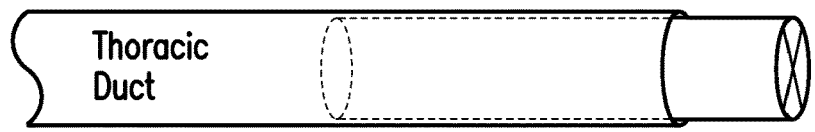
Figure 1E:
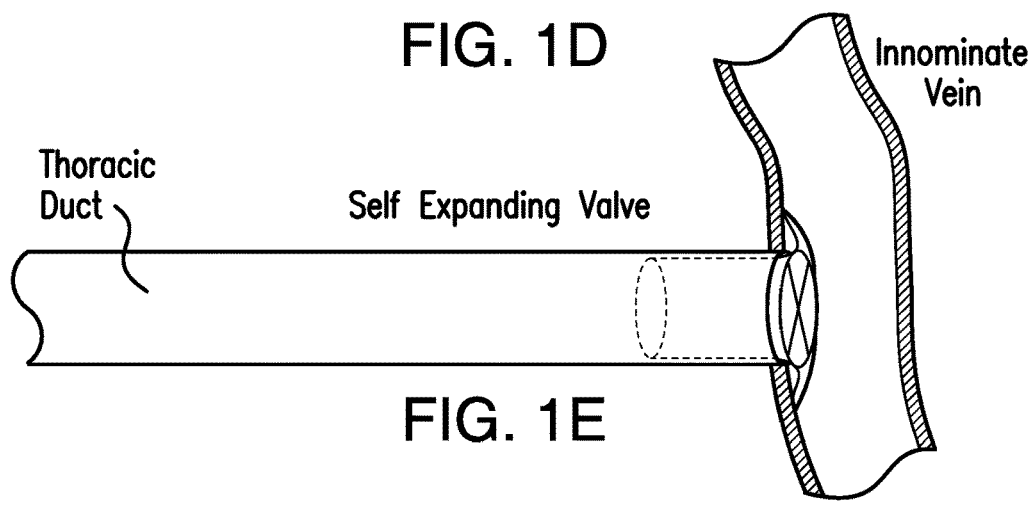

As shown in FIG. 1, in certain embodiments, the device can include a stent (see, for example, FIG. 1C). The stent can be of a type that requires application of a radially outward force such as by inflating a catheter balloon on which the stent is mounted, or alternatively, a self-expanding stent, which can automatically expand from a collapsed state. Non-limiting examples of stents are disclosed in PCT Patent Application No. WO1998/012989 and U.S. Pat. No. 8,147,538, the disclosures of which are hereby incorporated by reference in their entireties. Additional non-limiting examples of stents include self-expanding stents, balloon expanding stents, stent grafts, Wallstents, Palmaz-Schatz stents, Wiktor stents, Gianturco-Roubin stents, Cordis stents, AVE stents, coil stents and multilink stents.

In certain embodiments, the stent can have a diameter in the range of about 2 to about 20 mm and can have variable length. In certain embodiments, the stent can be a bare stent, e.g., a stent without a coating. For example, by not by way of limitation, the stent can be a bare-metal stent. In certain embodiments, the stent can be a covered stent, e.g., a stent with a coating, and/or a stent that is at least partially covered. For example, but not by way of limitation, the coating can only cover a portion of the stent, e.g., the proximal end, or can cover the inside and/or outside surfaces of the stent. Non-limiting examples of coatings include bio-engineered coatings, biological tissue coatings, biodegradable coatings, drug-eluting coatings, polymer-based coatings, e.g., polyethylene-based polymers, platinum coatings and diamond-like carbon coatings.

In certain embodiments, the device can include one or more valves to prevent the reflux of blood from the venous system into the thoracic duct (see FIGS. 1B, D and E). The valve can be of any type known in the art. For example, but not by way of limitation, the valve can have the configuration of a ball valve, a bicuspid valve, slit-like valve or a leaflet (e.g., trileaflet) valve. Additional non-limiting examples of valves include membrane type, solenoid, mechanical and biological valves. The position of the valve or valves can be anywhere in the stent, sheath, tubular element, vein or in the TD. In certain embodiments, the valve can be placed in the thoracic duct outlet.

Referring to FIG. 1, in certain embodiments, the valve and the stent can be incorporated in a single device (see FIG. 1B). In certain embodiments, the valve can be inserted in a previously implanted stent resulting in a single implanted device. Alternatively or additionally, the valve can be coupled to a tubular member or tissue engineered graft for implantation into a dilated thoracic duct and/or the thoracic duct outlet (see FIG. 1D).

In certain embodiments, the disclosed device can be implanted within the thoracic duct. In certain embodiments, the device can be positioned at the junction between the thoracic duct and the venous system. For example, the disclosed device for use in passively decompressing the lymphatic system can be deployed into the thoracic duct outlet and extend into the thoracic duct and/or the venous system, e.g., subclavian vein and/or the innominate vein (see FIG. 1A). In certain embodiments, the valve can be placed inside the thoracic duct and/or proximal to the thoracic duct/venous junction.

Devices for Active Decompression of the Lymphatic System

The presently disclosed subject matter also relates, in certain embodiments, to devices for monitoring and actively decompressing the lymphatic system. In certain embodiments, such active decompression is achieved using a pump-based system. In certain embodiments, this device can be used to change the unfavorable pressure gradients within the thoracic duct to decompress the lymphatic system. In certain embodiments, a device according to the disclosed subject matter can actively decompress the lymphatic system by alleviating unfavorable pressure gradients and, concomitantly, by alleviating limited flow capacity of the thoracic duct outlet value.

Figure 2:
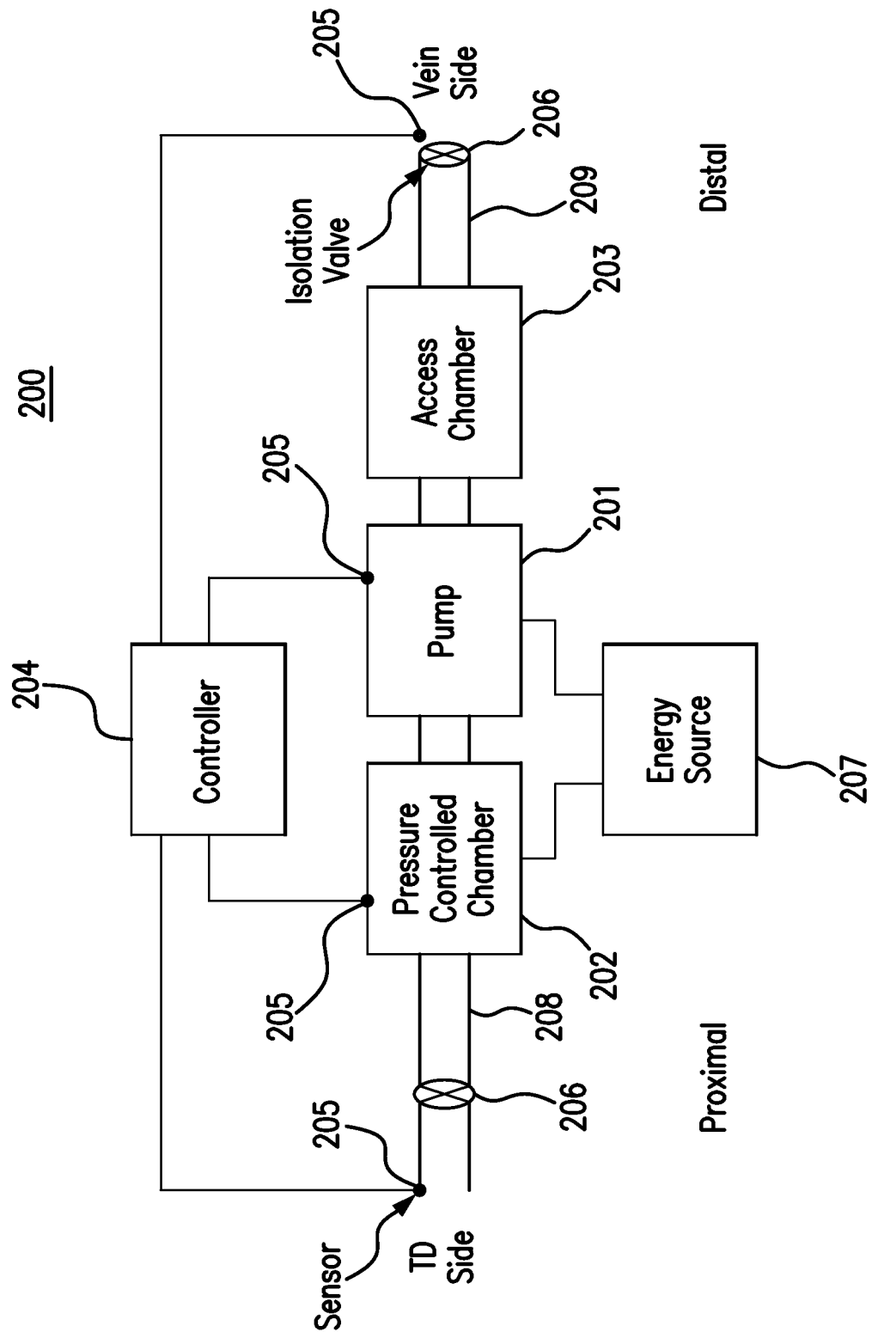
FIG. 2 is a schematic diagram depicting an exemplary device for actively decompressing the lymphatic system in accordance with one non-limiting embodiment of disclosed subject matter.

As shown in FIG. 2, in a certain non-limiting embodiment of a device in accordance with the disclosed subject matter, the device 200 can include a pump 201 that can function to actively remove lymphatic fluid from the thoracic duct. For example, and not by way of limitation, the pump 201 can be coupled to an inlet tubular member (also referred to herein as an inflow tubular member) that is placed within thoracic duct and an outlet tubular member (also referred to herein as an outflow tubular member) that is positioned with the venous system for pumping lymphatic fluid from the thoracic duct into the venous system. The fluid can be pumped from the thoracic duct continuously or intermittently. For example, the pump 201 can be, but is not limited to, a Piezo pump, a rotary pump, a peristalsis pump or a reciprocating pump. Non-limiting examples of a rotary pump include screw, progressing cavity pump, turbine, axial, lobe, centrifuge and axial rotary pumps. Non-limiting examples of reciprocating pumps include piston, plunger and diaphragm pumps. Additional non-limiting examples of pumps that can be used in the present disclosure are described in U.S. Pat. Nos. 8,591,478, 4,969,873, 6,589,198 and 8,034,030, the contents of which are incorporated by reference herein in their entireties.

The selection of the type of pump depends on the location of implantation, condition of the patient using the device and/or the patient's degree of need for assistance in the decompression of the lymphatic system. For example, but not by way of limitation, the pump can be sufficiently small, e.g., a micropump, to be implanted without the need for major invasive surgery and/or for implantation subcutaneously, within the thoracic duct or the thoracic duct/venous system junction.

In certain embodiments, the pump can pump lymphatic fluid at a rate of about 1 cc/min to about 100 cc/min. For example, the fluid flow rate of the pump can be from about 1 cc/min to about 90 cc/min, from about 1 cc/min to about 80 cc/min, from about 1 cc/min to about 70 cc/min, from about 1 cc/min to about 60 cc/min, from about 1 cc/min to about 50 cc/min, from about 1 cc/min to about 40 cc/min, from about 1 cc/min to about 30 cc/min, from about 1 cc/min to about 20 cc/min, from about 1 cc/min to about 10 cc/min, from about 1 cc/min to about 5 cc/min, from about 5 cc/min to about 100 cc/min, from about 10 cc/min to about 100 cc/min, from about 20 cc/min to about 100 cc/min, from about 30 cc/min to about 100 cc/min, from about 40 cc/min to about 100 cc/min, from about 50 cc/min to about 100 cc/min, from about 60 cc/min to about 100 cc/min, from about 70 cc/min to about 100 cc/min, from about 80 cc/min to about 100 cc/min or from about 90 cc/min to about 100 cc/min. In certain embodiments, the pump can pump lymphatic fluid at a rate equal to or greater than about 100 cc/min. In certain embodiments, the pump can pump fluid at a variable flow rate or a constant flow rate.

Figure 4A:
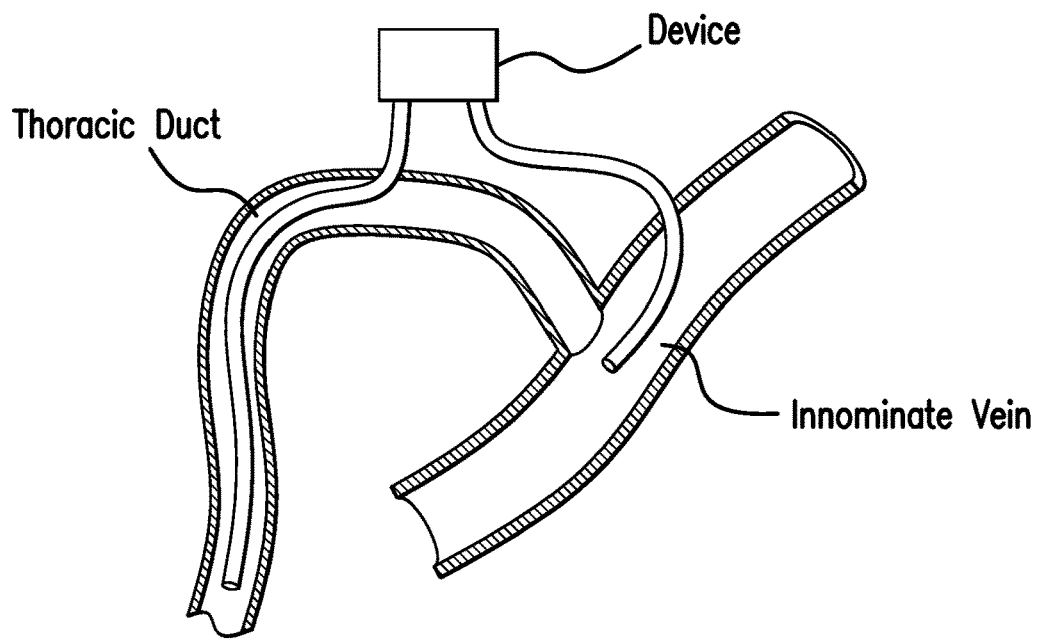
FIG. 4A-C depicts schematic diagrams showing the various locations of the device when deployed within a subject according to the presently disclosed subject matter.
Figure 4B:
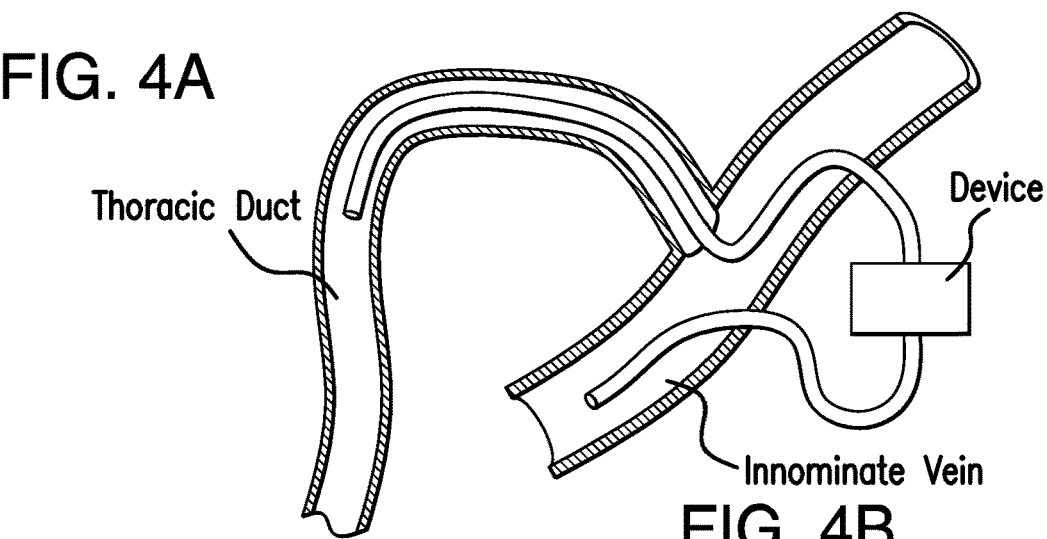
Figure 4C:
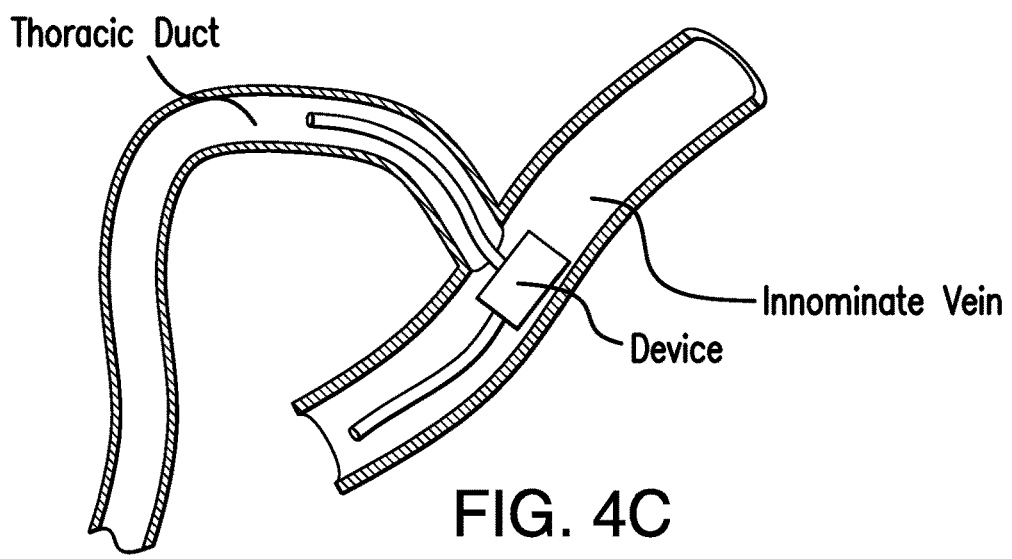
Figure 5A:
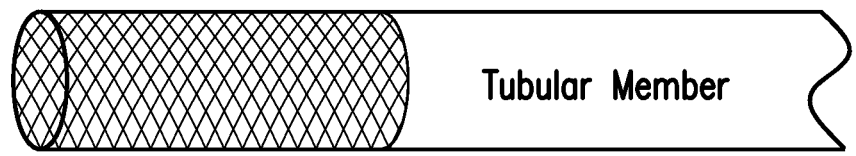
FIG. 5A-E depicts exemplary embodiments of stents or scaffolds for use with the disclosed devices according to the presently disclosed subject matter.
Figure 5B:
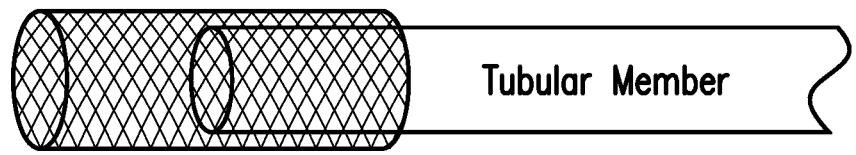
Figure 5C:
Figure 5D:
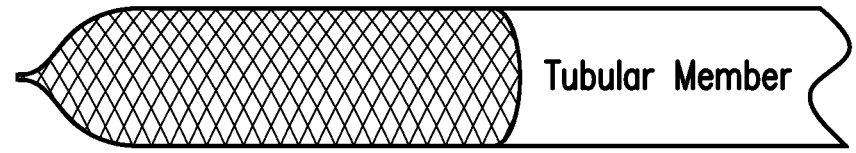
Figure 5E:
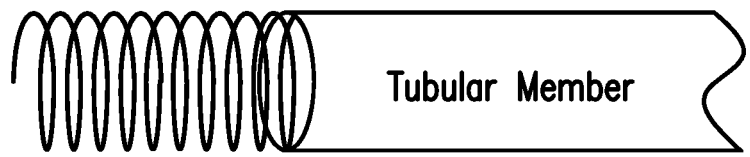

In certain embodiments, the pump 201 of the device 200 can be implanted internally, e.g., the pump 201 can be positioned within the thoracic duct. For example, but not by way of limitation, the pump 201 can be implanted within a stent that is positioned in the thoracic duct. Alternatively, the pump 201 can be positioned within the thoracic duct in the absence of a stent. In certain embodiments, the pump 201 can be positioned at the junction between the thoracic duct and the venous system. In certain embodiments, the pump 201 can be positioned at the thoracic duct/venous system junction within a stent or in the absence of the stent. Alternatively, the pump 201 can be positioned within the venous system (in the presence or absence of a stent), located external to the body of the subject, e.g., located on the surface of the subject's skin, under the skin (e.g., subcutaneously) or positioned adjacent to the thoracic duct and/or innominate vein (see FIG. 4). Non-limiting examples of stents are disclosed above.

In certain embodiments, the device 100 can further include a pressure controlled chamber 202 that can be regulated to maintain a pressure lower than the pressure within the thoracic duct. In certain embodiments, the pressure difference between the thoracic duct and the pressure controlled chamber 202 can drive the lymphatic fluid from the thoracic duct into the chamber. For example, the lower pressure within the pressure controlled chamber 202 can be maintained by, but not limited to, a mechanical spring, piston, elastic material, magnet, electromagnetic, pneumatic or by hydraulic pressure. The pressure controlled chamber 202 can be any device that has a lower pressure than the thoracic duct.

In certain embodiments, the device 200 can include two or more pressure controlled chambers 202, e.g., coupled in series. For example, the two or more pressure controlled chambers 202 can operate simultaneously to maintain a forward lymphatic flow. In certain embodiments, the two or more pressure controlled chambers 202 can be operated alternatively to maintain a forward lymphatic flow. In certain embodiments, the two or more pressure controlled chambers 202 can maintain different pressures. For example, but not by way of limitation, a pressure controlled chamber located furthest from the thoracic duct outlet can be programmed to maintain a higher pressure than a pressure controlled chamber located closer to the thoracic duct outlet to control the rate of flow and/or to ensure forward lymphatic flow towards the thoracic duct outlet and to control the rate of flow.

In certain embodiments, the pump 201 can be coupled to the pressure controlled chamber 202 and the pump 201 can function to remove the fluid from the pressure controlled chamber 202 into an access chamber 203. In certain embodiments, the pump 201 can include an inlet for receiving fluid from the pressure controlled chamber 202 and an outlet through which lymphatic fluid can be expelled towards and/or into the access chamber 203. The access chamber 203 can be positioned internally, subcutaneously and/or externally.

In certain embodiments, the access chamber 203 can serve as a port that can be accessed intermittently or continuously to remove a portion or all of the lymphatic fluid from the subject. For example, but not by way of limitation, if the access chamber 203 is located internally, then the chamber can be connected to a catheter that can be accessed externally for fluid sampling or fluid removal. In certain embodiments, some of the lymphatic fluid can be removed from the subject via the access chamber 203. For example, from about 1% to about 100% of the lymphatic fluid can be removed from the subject. In certain embodiments, from about 1% to about 95%, from about 1% to about 90%, from about 1% to about 85%, from about 1% to about 80%, from about 1% to about 75%, from about 1% to about 70%, from about 1% to about 65%, from about 1% to about 60%, from about 1% to about 55%, from about 1% to about 50%, from about 1% to about 45%, from about 1% to about 40%, from about 1% to about 35%, from about 1% to about 30%, from about 1% to about 25%, from about 1% to about 20%, from about 1% to about 15%, from about 1% to about 10%, from about 1% to about 5%, from about 5% to about 100%, from about 10% to about 100%, from about 15% to about 100%, from about 20% to about 100%, from about 25% to about 100%, from about 30% to about 100%, from about 35% to about 100%, from about 40% to about 100%, from about 45% to about 100%, from about 50% to about 100%, from about 55% to about 100%, from about 60% to about 100%, from about 65% to about 100%, from about 70% to about 100%, from about 75% to about 100%, from about 80% to about 100%, from about 85% to about 100%, from about 90% to about 100%, from about 95% to about 100%, from about 10% to about 80%, from about 20% to about 70%, from about 30% to about 60%, from about 40% to about 50% or from about 45% to about 50% of the lymphatic fluid can be removed from the subject.

In certain embodiments, the remaining lymphatic fluid within the access chamber 203 can be pumped into the venous system, e.g., though an outlet tubular member positioned within the venous system. In certain embodiments, at least a portion of the lymphatic fluid is pumped from the thoracic duct into the venous system to prevent clotting within the venous system and within the pump. In certain embodiments, some of the fluid that is removed can be modified and then returned to the venous system. In certain embodiments, an external fluid or substance can be inserted through the access chamber, e.g., through a catheter coupled to the access chamber, for the purpose of delivering a therapeutic, for preventing clotting or for other purposes.

In certain embodiments, the device 200 does not include an access chamber 203 and the lymphatic fluid can be pumped directly from the pressure controlled chamber 202 through a tubular member (e.g., catheter) into the venous system. For example, the pump 201 can include an inlet for receiving fluid from the pressure controlled chamber 202 and an outlet through which lymphatic fluid can be expelled towards and/or into the venous system in the absence of an access chamber 203.

In certain embodiments, the device 200 can include an energy source 207 for powering the components of the device 200. For example, and not by way of limitation, the energy source 207 can be used to power the pressure controlled chamber 202 and/or the pump 201. The energy source 207 can be internal, external and/or integrated into the implanted device 200. For example, but not by way of limitation, the energy power source 207 can be implanted subcutaneously and coupled to any one of the components of the device 200, e.g., the pump 201 and controller 204. The energy power source 207 can be rechargeable and/or inductive. Any energy source 207 known in the art can be used in the device. Non limiting examples of energy power sources are disclosed in U.S. Patent Application Nos. 2013/0320773 and 2009/0326597 and U.S. Pat. Nos. 8,630,717, 6,640,137, 7,729,768 and 5,810,015, the contents of which are hereby incorporated by reference in their entireties.

In certain embodiments, the device can include one or more isolation valves 206. For example, and not by way of limitation, the valves 206 can function to prevent the reflux of blood from the venous system into the thoracic duct and/or for preventing the flow of the lymphatic fluid into the pressure controlled chamber if decompression of the lymphatic system is not needed. The one or more isolation valves 206 of the device can be of any type known in the art. For example, one or more isolation valves 206 can be a membrane type, a solenoid, a leaflet, a ball, a mechanical, a biological valve or combinations thereof. The one or more isolation valves 206 can be of the same type or of different types.

In certain embodiments, a device 200 of the present disclosure can include a controller component 204. The controller 204 can function to control the one or more components of the device 200. For example, the controller 204 can function to control the activation, deactivation and/or pressure level of the pressure controlled chamber 202. Additionally or alternatively, the controller 204 can control the activation, deactivation and/or level of activity of the pump 201, e.g., flow rate, or the energy source 207. In certain embodiments, the controller 204 can control the activation, deactivation and/or level of activity of the one or more valves 206. The controller 204 can be located within the subject (i.e., internally) or can be positioned externally, and can communicate with the components of the device, e.g., pump 201, through a wired and/or wireless connection. For example, a controller 204 of the present disclosure can be located external to the body of the subject.

In certain embodiments, the device 200 can include one or more sensors 205. For example, but not by way of limitation, the one or more sensors 205 can be located in the thoracic duct, within the device, e.g., adjacent to the pressure controlled chamber 202 and/or pump 201, the venous system, e.g., subclavian vein and/or the innominate vein, at the junction between the thoracic duct and the venous system, at the junction between the device and the thoracic duct and/or at the junction between the device and the venous system. The sensors 205 can include, but are not limited to, pressure sensors, temperature, pH sensors, electrical sensors, piezo sensors, flow sensors, optical sensors, mechanical sensors, force sensors or transducers, blood sensors, infrared sensors, ultrasound sensors and/or volume or fluid level sensors. In certain embodiments, the sensors 205 can detect pressure and/or changes in pressure in the thoracic duct, the venous system and/or in the device. In certain embodiments, the sensors 205 can detect the chemical composition and/or changes in chemical composition of the lymphatic fluid (e.g., acidity, fat content and/or cell composition). In certain embodiments, the sensors 205 can detect flow volume and/or changes in flow volume in the thoracic duct, the venous system and/or in the device 200.

In certain embodiments, the one or more sensors 205 can function to monitor the pressure of the thoracic duct and be in communication with the controller 204 of the device 200. In certain embodiments, the sensor 205 can signal to the controller to indicate when decompression of the lymphatic system is necessary. For example, the sensor 205 can signal to the controller 204 when the pressure of the thoracic duct pressure is sufficiently high to require flow of the lymphatic fluid into the pressure controlled chamber 202. In certain embodiments, the detection of a specific indicator, e.g., a specific pressure threshold, can result in the opening of the pressure controlled chamber 202 to allow fluid to pass into the chamber. Alternatively or additionally, the sensor 205 can be coupled to one or more isolation valves 206, where detection of a specific indicator, e.g., a specific pressure threshold, results in the opening of a valve to allow fluid to pass from the thoracic duct into the pressure controlled chamber 202. In certain embodiments, the device 200 can include an isolation valve 206 that functions to isolate the device from the blood of the venous system and/or the lymphatic fluid as discussed above. In certain embodiments, the detection of a specific indicator, e.g., a specific pressure threshold, can result in the activation of the pump 201 to pump fluid from the pressure controlled chamber 202 to the access chamber 203 and/or the venous system. Alternatively or additionally, the detection of a specific indicator, e.g., a specific pressure threshold, can result in a change in the rate at which the pump moves fluid from the pressure controlled chamber 202 to the access chamber 203 and/or the venous system, e.g., an increase in the flow rate. The specific pressure threshold at which the device and/or device components can be activated and/or opened depends on the condition of the patient and the type of disease the patient using the device is suffering from.

The one or more sensors 205 can communicate directly with the pressure controlled chamber 202, pump 201 and/or valves 206 or indirectly through the controller 204. For example, but not by way of limitation, information from the sensor 205 can be communicated to the controller 204 which can then activate the pump 201. In certain embodiments, if the pressure in the thoracic duct is greater than the pressure in the venous system, e.g., subclavian vein and/or the innominate vein, the pump 201 can be activated to remove fluid from the pressure controlled chamber 202.

In certain embodiments, the device 200 can include tubular elements (also disclosed herein as tubular members; see 208 and 209 of FIG. 2). For example, and not by way of limitation, the device can include tubular members that connect the components of the device together, and can also allow the device to have a central lumen through which the lymphatic fluid can flow. In certain embodiments, the component at the proximal end of the device 200, e.g., the pressure controlled chamber 202, is connected to the thoracic duct through a tubular element (also referred to herein as an inflow or inlet tubular member; see 208 of FIG. 2), and a component at the distal end, e.g., the access chamber 203 or pump 201, is connected to the venous system through a second tubular element (also referred to herein as an outflow or outlet tubular member; see 209 of FIG. 2).

In certain embodiments, the device can have an additional lumen that can connect to the inflow tubular member 208 or the outflow tubular member 209 for delivery of therapeutics or for fluid removal. In certain embodiments, a lumen of the device, e.g., a lumen of one or more tubular members of the device, can collapse in the absence of lymphatic fluid flow. Collapse of the device's lumen can prevent blood from flowing from the venous system into the device and/or lymphatic system. For example, and not by way of limitation, the tubular members of the device can include a collapsing chamber, which can be compressed externally or internally.

In certain embodiments, the tubular element inside the thoracic duct (i.e., inflow tubular member; see 208 of FIG. 2) and/or the tubular element within the venous system (i.e., the outflow tubular member; see 209 of FIG. 2) can have an anchoring element or support structure, such as a balloon-expanding structure, scaffold or self-expanding structure (see FIG. 5). In certain embodiments, a tubular element of an embodiment of the disclosed device can include a stent that is coupled to its free end. Non-limiting examples of stents are disclosed above. For example, and not by way of example, the stent can surround the tubular member or can be adjacent to the tubular member (see FIGS. 5A-E). In certain embodiments, such structures can be used to keep the thoracic open and unobstructed and/or can serve to provide a scaffold for the coupled tubular member. In certain embodiments, the tubular elements 209 and 208 can be perforated to allow better flow of lymph fluid into the element.

In certain embodiments, the device can further include one or more ports that can be accessed intermittently or continuously. The port can be located at any location on the device. For example, and not by way of limitation, the port can be accessed externally by the presence of a catheter (or tubular member) that is coupled to the port. Alternatively or additionally, the port can be accessed percutaneously. Non-limiting examples of ports that can be present on the device include self-healing ports. In certain embodiments, the port can be used to introduce therapeutics into the device and/or the venous system of the subject (e.g., in the case of an occlusion). Non-limiting examples of therapeutics that can be introduced through a port present within the device include anti-coagulants such as factor Xa inhibitors, heparin and tissue plasminogen activator (tPA). In certain embodiments, the port can be used to flush the device and/or the one or more tubular members of the device.

In certain embodiments, the device can further include a component that is located proximally to the pump 201 for preventing the accumulation of protein within the pump 201. For example, and not by way of limitation, the device can include rotating blades that can function to break down protein that is present in the lymph fluid prior to entrance of the fluid into the pump 201.

In certain embodiments, the device can further include a chamber that can be compressed to promote the flow of the lymphatic fluid from the thoracic duct into to the venous system. The compressible chamber can be included in a device that includes a pump. The chamber can be located internally, e.g., positioned subcutaneously, or can be located externally to the subject's body. In certain embodiments, the chamber can be compressed externally to promote forward fluid flow.

The internal location, e.g., implantation site, of the device and/or the components of the device can vary depending on the method by which the device/components are to be implanted and/or delivered. For example, and not by way of limitation, the device and/or components of the device can be delivered percutaneously or transcutaneously. In certain embodiments, a device of the disclosed subject matter can be placed within the thoracic duct. In certain embodiments, the device can be placed at the junction between the thoracic duct and the venous system, such that part of the device is within the thoracic duct and another part of the device is within the venous system, or located within the venous system (see, for example, FIG. 4C).

In certain embodiments, the components of the disclosed device, e.g., the pump and/or the sensors, can be located within distinct regions of the body of a subject or external to the body of the subject. For example, the pump 201 can be implanted subcutaneously and coupled to a pressure controlled chamber 202 that is located within the thoracic duct. In certain embodiments, the inflow tubular member 208 can be positioned within the thoracic duct and the outflow tubular member 209 can be placed in the venous system, e.g., within the innominate vein (see FIG. 4). In certain embodiments, the remaining components of the device can be located externally to the thoracic duct and/or the venous system (see, for example, FIGS. 4A and B). For example, and not by way of limitation, the remaining components of the device can be located external to the body of the subject, e.g., on the surface of the skin of the subject, subcutaneously and/or adjacent to the thoracic duct and/or the venous system. Alternatively, the remaining components of the device can be located within the thoracic duct and/or the venous system (see, for example, FIG. 4C).

Any or all components of the devices described herein can be made from, for example, single or multiple stainless steel alloys, nickel titanium alloys, cobalt-chrome alloys, nickel-cobalt alloys, molybdenum alloys, tungsten-rhenium alloys, polymers such as polyethylene teraphathalate (PET), polyester, polyester amide, polypropylene, aromatic polyesters, such as liquid crystal polymers, ultra high molecular weight polyethylene fiber and/or yarn, polytetrafluoroethylene (PTFE), expanded PTFE (ePTFE), polyether ketone (PEK), polyether ether ketone (PEEK), polyether ketone ketone (PEKK), nylon, polyether-block co-polyamide polymers, aliphatic polyether polyurethanes, polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials or combinations thereof. Non-limiting examples of radiopaque materials are barium sulfate, zinc oxide, titanium, stainless steel, nickel-titanium alloys, tantalum, and gold. Alternatively or additionally, one or more components of the disclosed devices can be made from a biomaterial or coated with a biomaterial. Non-limiting examples of a biomaterial include tissue, collagen, allograft, autograft, heterograft, xenograft, bone cement, morselized bone, osteogenic powder and beads of bone. Alternatively or additionally, one or more components of the disclosed devices can be coated with a polymer, chemical or biomaterial to make it more biocompatible or hydrophilic, or to prevent deposition of lipids or protein onto the walls and/or surfaces of the device.

Methods of Use

The presently disclosed subject matter further relates, in certain embodiments, to methods for alleviating the central lymphatic congestion using one or more of the devices disclosed above. For example, but not by way of limitation, the present disclosure provides, in certain embodiments, methods for delivery of the disclosed devices within the thoracic duct.

Figure 3:
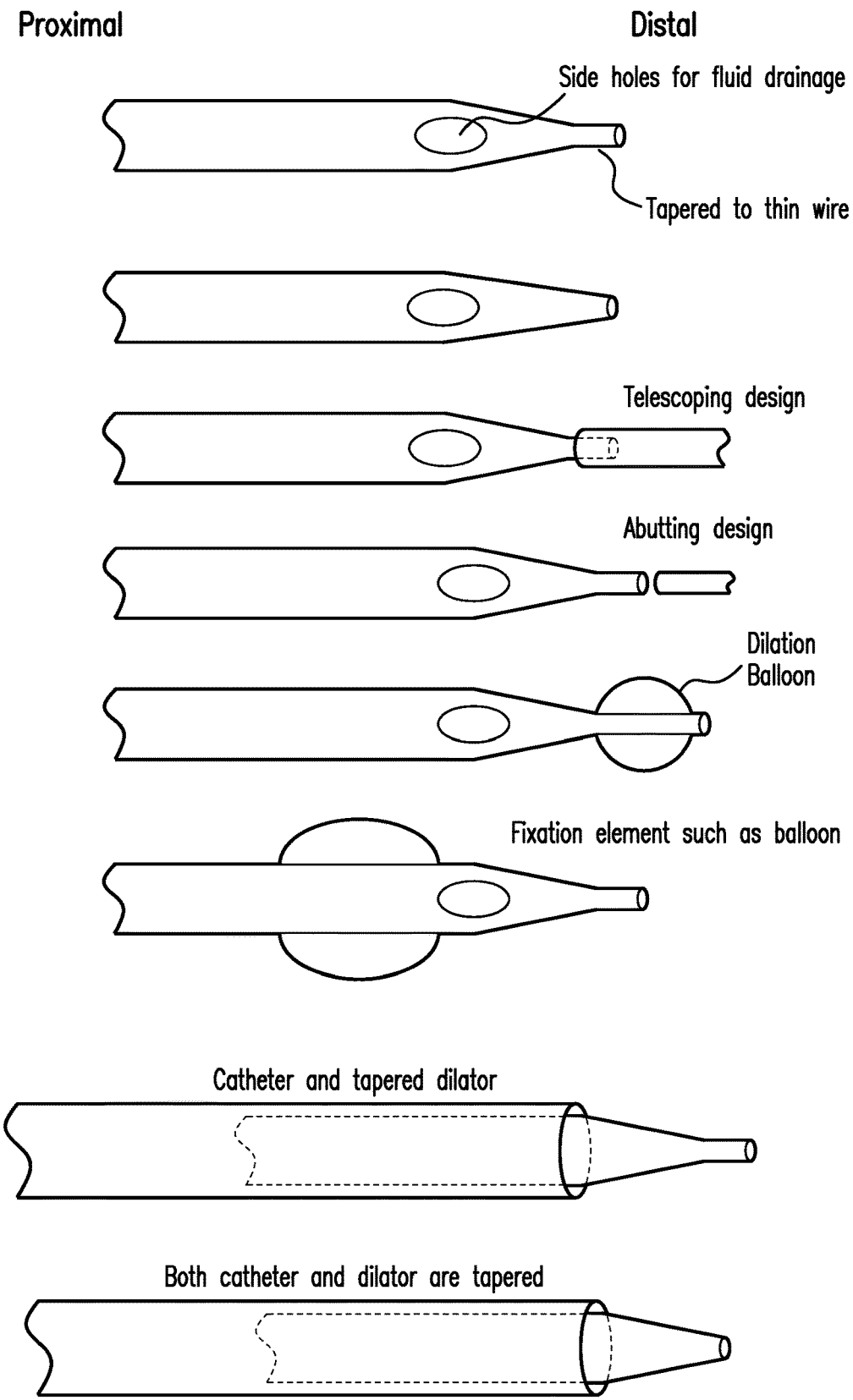
FIG. 3 depicts exemplary embodiments of methods for deploying the disclosed devices according to the presently disclosed subject matter.

In certain embodiments, the implantation of a device of the present disclosure can be accomplished using minimally invasive techniques. By using such techniques, the complications associated with open surgery, e.g., higher risks of infection and longer recovery times, can be avoided. For example, a device disclosed herein can be inserted into the venous system, e.g., subclavian vein, percutaneously. In certain embodiments, the device can be inserted into the venous system and guided through the venous system to access the thoracic duct. For example, the method can include the use of a delivery catheter and/or a tubular member (see FIG. 3) to deliver the device to the thoracic duct and/or thoracic duct outlet. In certain embodiments, the tubular members, e.g., the outflow tubular member and/or the inflow tubular member, can include outlets (or ports) positioned near the distal end of the member to allow fluid drainage after implantation of the device.

In certain embodiments, a device disclosed herein can be inserted into the thoracic directly, without entering the venous system. For example, and not by way of limitation, the device can be inserted into the thoracic duct surgically, transcutaneously or percutaneously. In certain embodiments, the device can be inserted into the thoracic duct and guided through the thoracic duct for proper placement. As disclosed above, the method can include the use of a wire, delivery catheter and/or a tubular member (see FIGS. 3 and 4) to deliver the device to the thoracic duct and/or thoracic duct outlet. In certain embodiments, the wire, delivery catheter and/or a tubular member can be inserted into the thoracic duct retrograde or anterograde and can be used to guide the device to its proper location. In certain embodiments, one or more components of the device can be inserted into the thoracic duct directly and one or more components of the device can be inserted into the venous system, e.g., innominate vein, directly.

In certain embodiments, the tubular member used for delivering the device is tapered at its distal end. In certain embodiments, the tubular member is tapered to a thin wire at its distal end, where the wire can assist in guiding the tubular member through the venous system. For example, a device that includes a self-expanding stent can be deployed by advancing the stent out of an end of a tubular member, e.g., a delivery catheter, at the site of implantation. In certain embodiments, the method can include the use of a retractable sheath coupled to the tubular member to implant the device. In certain embodiments, a device can be positioned inside a tubular member and internally implanted by unsheathing of an outer sheath from the tubular member. For example, a device that includes a stent can be deployed by the retraction of an outer sheath from a tubular member that restrained the self-expanding stent in its collapsed state. Alternatively or additionally, a device can be positioned at the tip of a tubular member and delivered to the site of implantation, e.g., the junction between the thoracic duct and the venous system.

In certain embodiments, the method can include dilating the thoracic duct outlet prior to implantation of the device. The thoracic duct outlet can be dilated through the use of a stent, a balloon, a dilator and other expanding devices. For example, but not by way of limitation, the method for delivery of a device disclosed herein can include the use of a tubular member that includes a balloon and/or dilator to dilate the thoracic duct outlet, and deliver the device to the site of dilation. In certain embodiments, the dilator is tapered at its distal end.

In certain embodiments, the method can include the separate delivery of one or more components of a device to the site of implantation followed by the assembly of the device at the site of implantation. For example, the method can include the delivery of the pressure controlled chamber followed by the delivery of the pump, where coupling of these two components to generate an integrated device can occur at the site of implantation.

In certain embodiments, the devices of the disclosed subject matter can be disposable and deployed within a stent or a tubular element and can be easily retrieved and replaced. In certain embodiments, the device can have an open pathway that allows for passive decompression and, in addition, can have an active pathway that passes through the pressure controlled chamber and the pump for additional active decompression when needed.

The following example is offered to more fully illustrate the disclosure, but is not to be construed as limiting the scope thereof.

Example 1: Active Decongestion of the Lymphatic System

Figure 6:
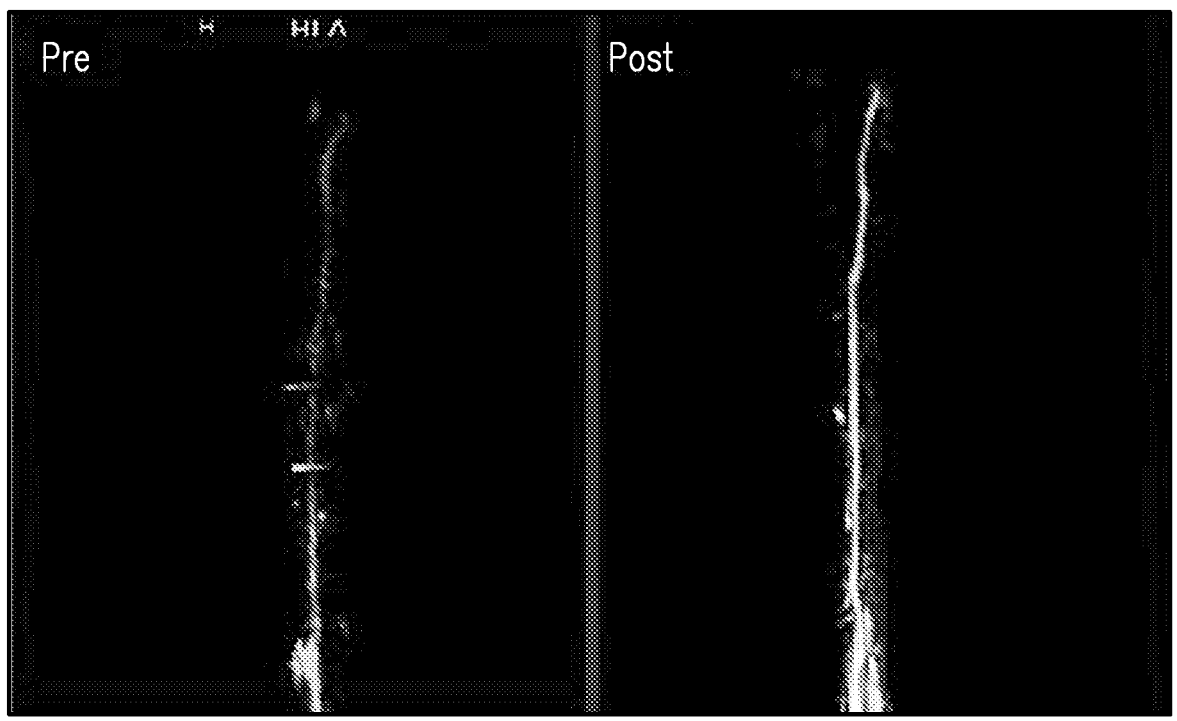
FIG. 6 depicts magnetic resonance imaging (MRI) of the thoracic duct prior to heart failure (left panel) and after heart failure (right panel).

In this Example, a pump-based device was used to actively decompress the thoracic duct in an animal model of severe tricuspid regurgitation. The animal model of severe tricuspid regurgitation was prepared by destroying the tricuspid valve of a 40-50 lb swine using a custom made catheter. The degree of tricuspid valve regurgitation was confirmed by pressure measurement in the right atrium and using angiography. The animal was allowed to recover and then observed for 3 months. During this time the degree of right-sided heart failure was periodically evaluated using cardiac catheterization and cardiac magnetic resonance imaging (MRI) studies. At 3 months, the animal displayed signs of right-sided heart failure including elevated central venous pressure (CVP), liver enlargement, tissue edema and ascites. The animal was then taken to the MRI scanner for quantification of ascites and evaluation of the thoracic duct. As shown in FIG. 6, the diameter of the thoracic duct is enlarged during right-sided heart failure (right panel) as compared to the diameter of the thoracic duct prior to heart failure (left panel).

Figure 7:
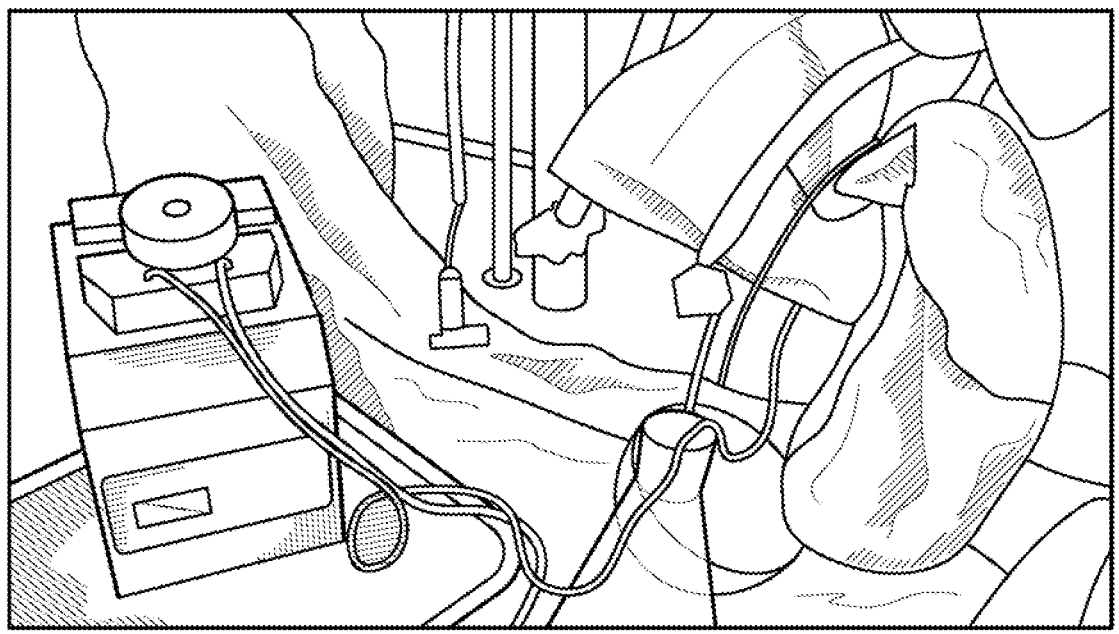
FIG. 7 depicts the device used to actively drain the thoracic duct in an animal model of right-sided heart failure.

As shown in FIG. 7, the device included an external peristaltic pump coupled to an inlet tubular member (i.e., an inflow tubular member) that was placed into the thoracic duct and an outlet tubular member (i.e., an outflow tubular member; also coupled to the pump) that was placed in the venous system. To install the device, in a cardiac catheterization laboratory anterograde thoracic duct cannulation was achieved using a micro catheter and V-18 wire. The wire was externalized through the right innominate vein and then over the wire a 5 French Flexor sheath was inserted retrograde into the distal thoracic duct. The sheath was then connected to a peristaltic pump and from there to a venous line that was positioned in the external jugular vein. Decompression of the thoracic duct was initiated at the rate of 1.5 L per hour and continued for 4 hours. During the decompression of the thoracic duct, pressure measurements were obtained in the thoracic duct and in the right atrium. After 4 hours, the animals were taken to the MRI scanner for quantification of ascites.

Figure 8A:
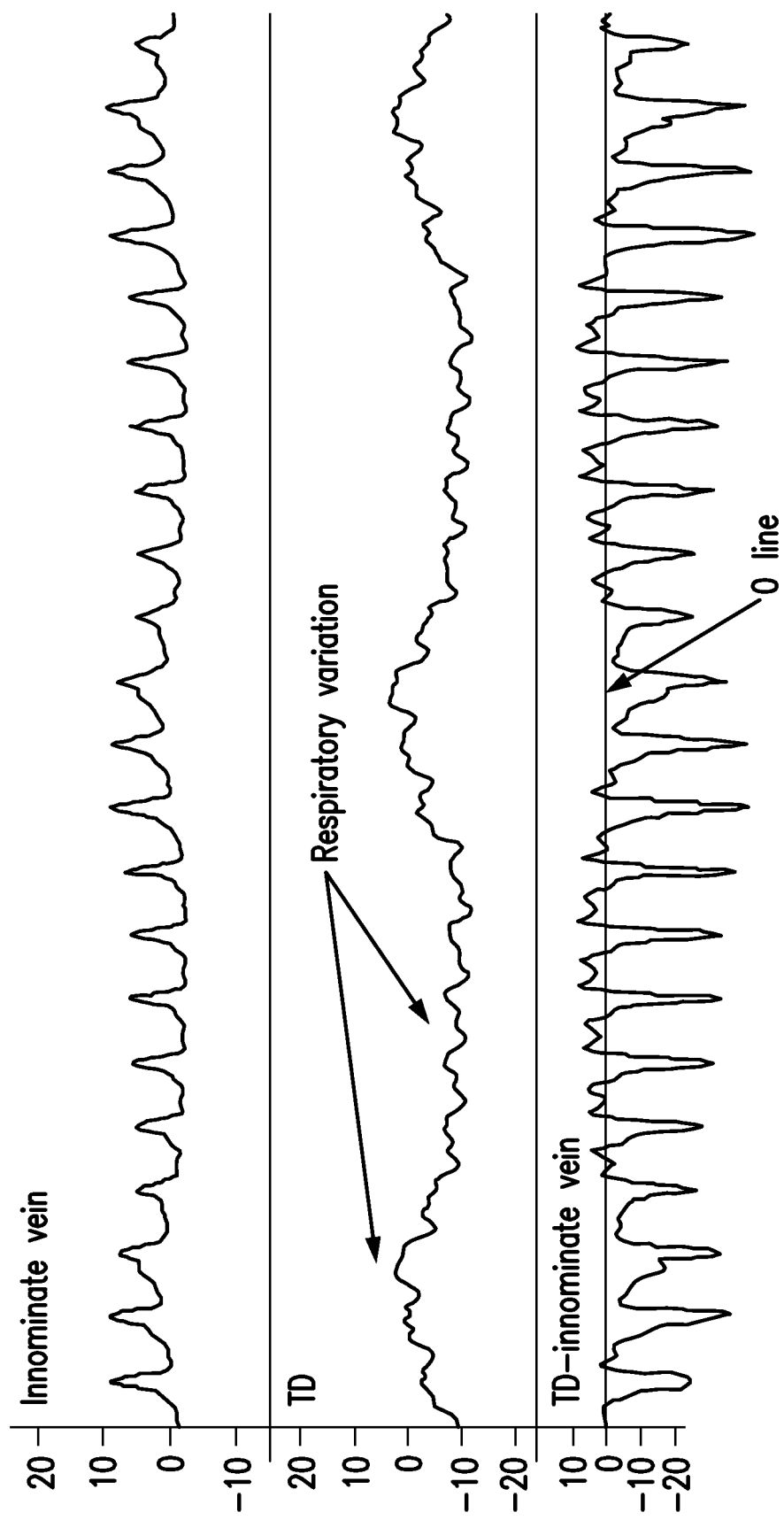
Figure 8B:
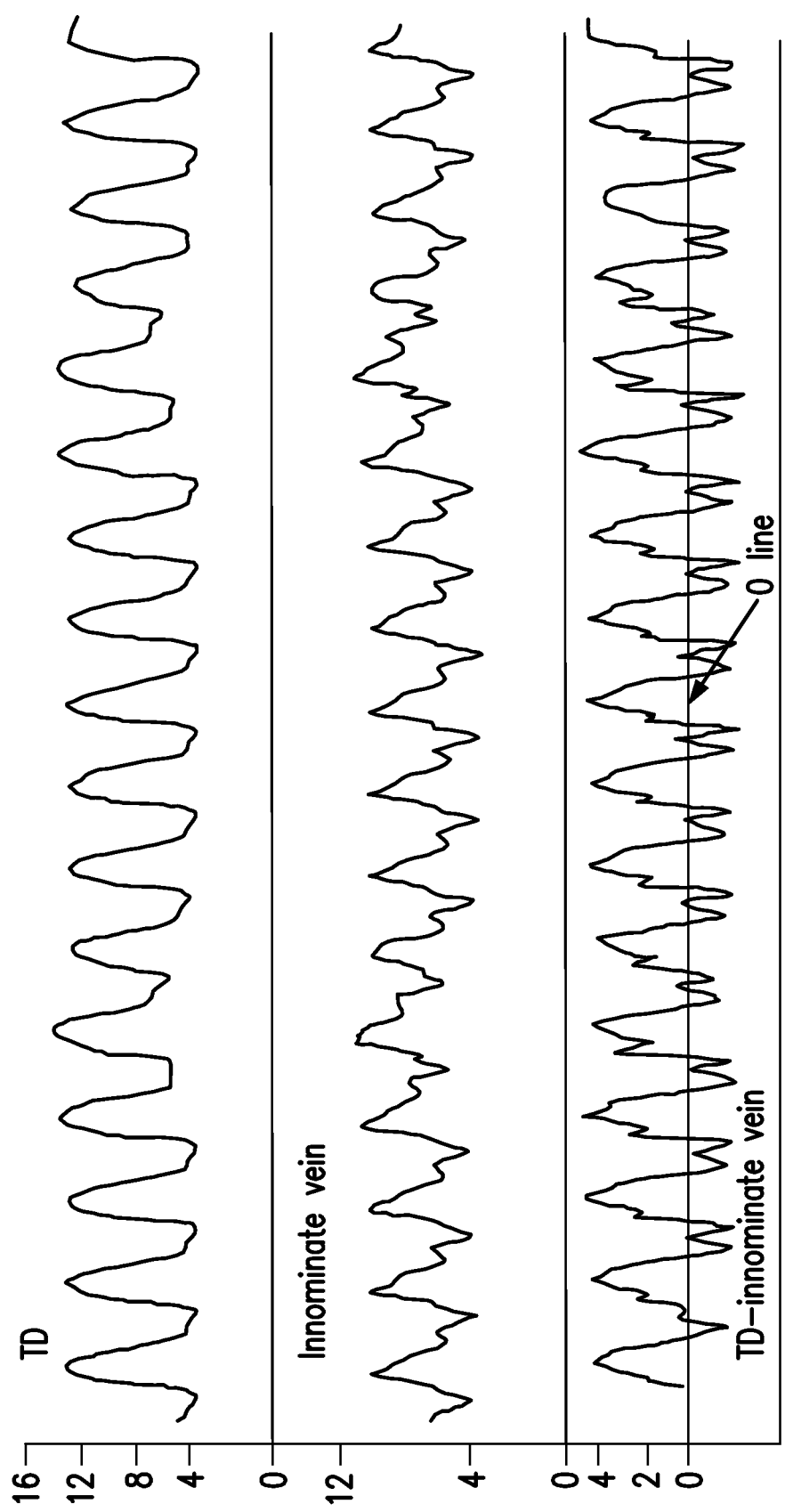
Figure 8C:
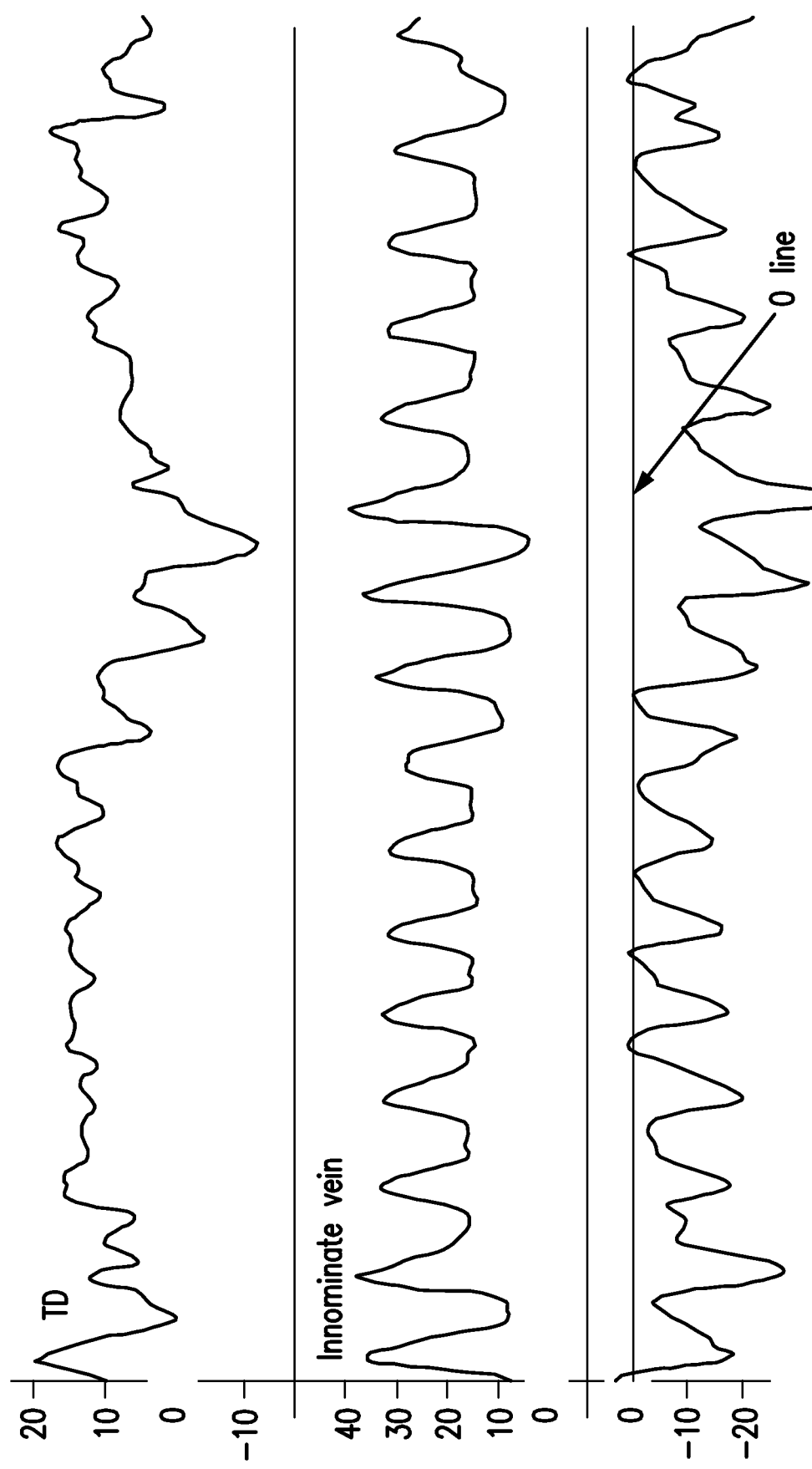
Figure 9:
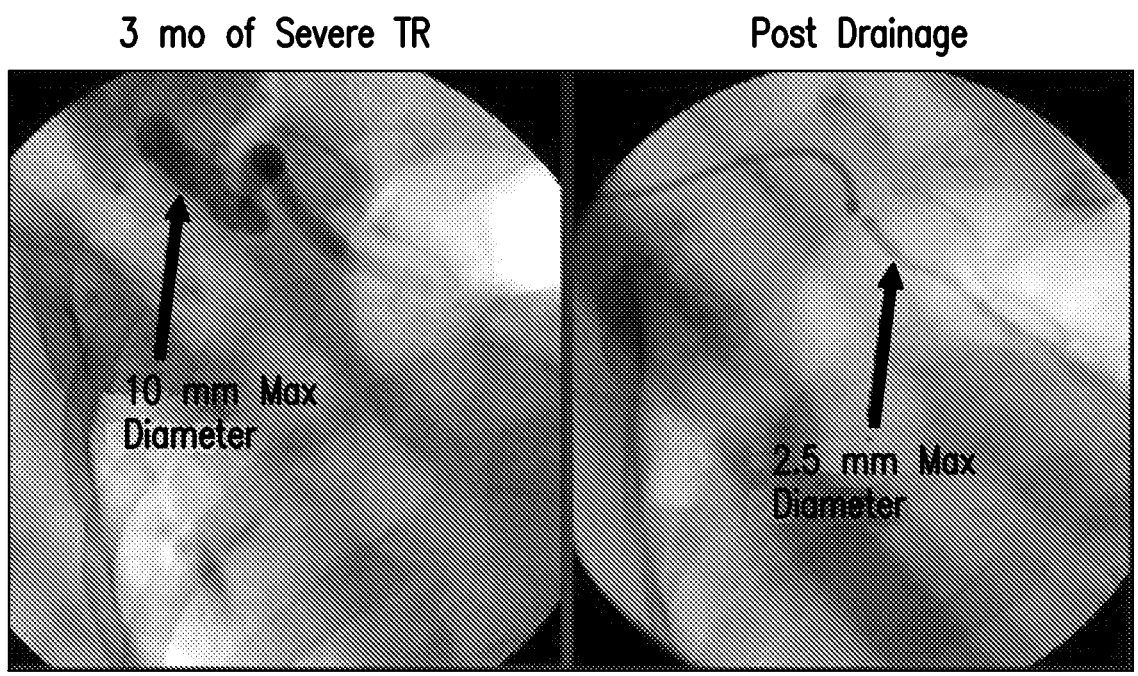
FIG. 9 depicts the effect of thoracic duct drainage on thoracic duct size.

In a normal animal, the pressure of the thoracic duct was non-pulsatile and the difference between the pressure of the thoracic duct and the innominate vein (ΔP) was negative through most of the cardiac cycle (FIG. 8A). In contrast, in an animal that has heart failure, the pressure of the thoracic duct was pulsatile and was significantly higher than the venous pressure throughout most of the cardiac cycle (FIG. 8B), which resulted in the failure of the lymphatic system resulting in ascites. As shown in FIG. 8B, the difference between the pressure of the thoracic duct and the innominate vein (ΔP) was mostly positive (FIG. 8B). The thoracic duct diameter was also significantly dilated, measuring about 10 mm (FIG. 9, left panel). Following four hours of actively draining the lymphatic system and recirculation of the lymph back into venous circulatory system, the animal's urine output increased significantly. In addition, the pressure of the thoracic duct became lower than the venous pressure throughout most of the cardiac cycle and the difference between the pressure of the thoracic duct and the innominate vein (ΔP) was mostly negative (FIG. 8C), similar to the results observed in a normal animal (see FIG. 8A).

The active drainage of the lymphatic system further resulted in the reduction in the ascites volume of about 50% from about 3 liters to about 1.75 liters (FIG. 8D). As shown in FIG. 9, active drainage of lymph fluid from the lymphatic system to the venous system resulted in the reduction of the diameter of the thoracic duct to a maximum diameter of 2.5 mm (which is similar to normal animals; right panel) as compared to the diameter of the thoracic duct prior to drainage (maximum diameter of about 10 mm; left panel). These results show that active drainage of the lymphatic system using a pump-based device can alleviate the congestion of lymphatic system and reduce ascites.

REFERENCES

1. Ludwig J, Linhart P, Baggenstoss A H. Hepatic lymph drainage in cirrhosis and congestive heart failure. A postmortem lymphangiographic study. Archives of pathology. 1968 Nov. 1; 86(5):551-62.
2. Witte M H, Dumont A E, Clauss R H, Rader B, Levine N, Breed E S. Lymph circulation in congestive heart failure: effect of external thoracic duct drainage. Circulation. 1969 Jun. 1; 39(6):723-33.
3. Uheley H N, Leeds S E, Sampson J J, Friedman M. Right Duct Lymph Flow in Experimental Heart Failure Following Acute Elevation of Left Atrial Pressure. Circulation Research. 1967 Mar. 1; 20(3):306-10.
4. Fish J C, Sarles H E, Remmers A R, Williams R D. Effect of Thoracic Duct Decompression on Ascites. JAMA. American Medical Association; 1968 Jan. 8; 203(2):98-102.
5. Akcay F, Ackerman N B. Effects of operative manipulation on the flow of intestinal lymphatics. Am. J Surg. 1971 November; 122(5):662-5.
6. Schreiber H W, Koch W, Ackeren von H, Georgi T, Schilling K. Cervicallymphovenous anastomosis for portal hypertension in cirrhosis of the liver. Ger Med Mon. 1968 August; 13(8):361
7. Cole W R, Witte M H, Kash S L, Rodger M, Bleish V R, Muelheims G H. Thoracic Duct-to-Pulmonary Vein Shunt in the Treatment of Experimental Right Heart Failure. Circulation. 1967 Oct. 1; 36(4):539-43.

Although the presently disclosed subject matter and its advantages have been described in detail, it should be understood that various changes, substitutions and alterations can be made herein without departing from the spirit and scope of the presently disclosed subject matter as defined by the appended claims. Moreover, the scope of the presently disclosed subject matter is not intended to be limited to the particular embodiments described in the specification. Accordingly, the appended claims are intended to include within their scope such modifications. Various references are cited herein, the contents of which are hereby incorporated by reference in their entireties.

We claim:

1. A device for reducing congestion of a lymphatic system comprising:
   a. an inlet tubular member;
   b. a pump coupled to the inlet tubular member;
   c. an outlet tubular member coupled to the pump;
   d. a controller coupled to the pump;
   e. a first sensor coupled to the controller, and
   f. a second sensor coupled to the controller,
wherein the first sensor is configured to detect pressure in a thoracic duct,
wherein the second sensor is configured to detect pressure in a venous system, and
wherein an increase in pressure detected by the first sensor results in the activation of the pump by the controller to transfer lymph fluid from the lymphatic system via the inlet tubular member to the venous system via the outlet tubular member.

2. The device of claim 1, further comprising a pressure controlled chamber, coupled to the inlet tubular member and the pump, for providing a favorable pressure gradient for flow of the lymph fluid from the lymphatic system.

3. The device of claim 2, further comprising an access chamber, coupled to the outlet tubular member and the pressure controlled chamber, wherein the activation of the pump results in the flow of lymph fluid from the pressure controlled chamber to the access chamber.

4. The device of claim 1, further comprising an isolation valve, coupled to the outlet tubular member, wherein the isolation valve functions to isolate the device from blood of the venous system.

5. A method for reducing the congestion of the lymphatic system comprising:
   a. providing a tapered tubular member;
   b. coupling a device of any of the claims 1-4 to the tubular member,
   c. guiding the coupled tubular member and device to a site of implantation;
   d. implanting the device at the site of implantation; and
   e. removing the tapered tubular member.

6. The method of claim 5, wherein the coupled tubular member is guided through the venous system to the thoracic duct outlet.

7. The method of claim 5, wherein the coupled tubular member is guided through the venous system through the thoracic duct outlet and into the thoracic duct.

8. The method of claim 5, wherein the coupled tubular member is guided through the thoracic duct to the thoracic duct outlet.

9. The method of claim 5, wherein the site of implantation is the junction between the venous system and the thoracic duct.

10. The method in claim 5, wherein the site of implantation is under the skin.

11. The method in claim 5, wherein at least one component of the device sits on top of the skin.

12. The method in claim 5, wherein the device is delivered transcutaneously directly into the thoracic duct.

* * * * *